United States Patent [19]

Bales et al.

[11] Patent Number: 4,726,374
[45] Date of Patent: Feb. 23, 1988

[54] LEAKPROOF HEMOSTASIS VALVE

[75] Inventors: Thomas O. Bales, Coral Gables; J. William Box, Miami; Keith Reisinger, Miami Lakes, all of Fla.

[73] Assignee: Cordis Corporation, Miami, Fla.

[21] Appl. No.: 73,859

[22] Filed: Jul. 15, 1987

Related U.S. Application Data

[63] Continuation of Ser. No. 806,526, Dec. 9, 1985, abandoned.

[51] Int. Cl.⁴ .............................................. A61M 29/02
[52] U.S. Cl. .................................. 128/344; 128/348.1; 604/256; 277/110
[58] Field of Search ................... 604/256, 167, 9, 169, 604/30, 247, 248; 277/110–112; 128/348.1, 344

[56] References Cited

U.S. PATENT DOCUMENTS

| | | | |
|---|---|---|---|
| 3,180,334 | 4/1965 | Glenn | 604/276 |
| 4,000,739 | 1/1977 | Stevens | 604/280 |
| 4,177,814 | 12/1979 | Knepshield et al. | 604/167 X |
| 4,240,411 | 12/1980 | Hosono | 604/167 X |
| 4,424,833 | 1/1984 | Spector et al. | 604/167 X |
| 4,430,081 | 2/1984 | Timmermans | 604/256 |

*Primary Examiner*—Michael H. Thaler
*Attorney, Agent, or Firm*—George H. Gerstman

[57] ABSTRACT

A hemostasis valve, for example, for a catheter for entering coronary blood vessels. The valve defines an adjustable high pressure seal and a second seal of typically lower pressure resistance.

5 Claims, 4 Drawing Figures

LEAKPROOF HEMOSTASIS VALVE

This application is a continuation of U.S. application Ser. No. 806,526, filed Dec. 9, 1985 now abandoned.

BACKGROUND OF THE INVENTION

Hemostasis valves are currently used on catheters for performing percutaneous transluminal coronary angioplasty (PTCA), as well as angiographic procedures, for example, where X-ray contrast fluid is inserted into the coronary artery.

In PTCA, stenotic regions of coronary blood vessels are dilated by advancing a dilatation catheter through blood vessels into the stenotic region. The dilatation catheter advances over a guide wire, which guide wire moves forward, followed by the catheter, followed by another advance of the guide wire, etc. The guide wire-dilatation catheter system may be introduced through a guiding catheter to facilitate its placement.

To prevent the leakage of blood out of the proximal end of the catheter, a hemostasis valve is provided at the proximal end, to prevent seepage of blood between the guide wire and the catheter. For example, currently, numerous types of hemostasis valves are known. See for example Stevens, U.S. Pat. No. 4,000,739. Another design of hemostasis valve is the Tuohy-Borst type, making use of an adjustable, compressive sleeve which is axially compressed about the guide wire that it seals by means of a two-piece, screw threaded housing. Other designs may use an "O" ring and a tapered seat instead of a sleeve.

Many designs require tightening of the valve when high pressure X-ray contrast fluid or the like is run through the catheter. However, with such high pressure sealing, the guide wire cannot be advanced in effective manner, so the valve, such as a Tuohy-Borst valve, must be loosened so that the operator can "feel" any resistance encountered by the forward advancement of the guide wire, during the operation of advancing the guide wire through blood vessels.

The degree of loosening of the valve can be critical. If excessively loosened, low pressure leakage may occur. If loosened too little, the guide wire cannot be effectively advanced. Accordingly, it turns out that for the most effective performance of PTCA and angiography procedures, a hemostasis valve which is highly controllable is needed, so that the guide wire can be easily advanced, while low pressure leakage is prevented on an easy, reliable basis, without the need for great skill and experience in operation of the valve.

By this invention, a hemostasis valve is provided with reliable sealing against low pressure leakage around a guide wire or the like. At the same time an adjustable seal is also provided which may be adjusted to seal against high pressures. Accordingly, the adjustable seal may be applied or released as desired, but, preferably, a low pressure seal may be constantly present to stop leakage upon release of the high pressure seal. Thus, manipulation of the high pressure seal is less critical, and requires less skill in order to avoid leakage.

Also, the surgeon who is manipulating a typical catheter for entering coronary blood vessels, for example, is overburdened with respect to things to hold and manipulate during this process. By this invention, improved efficiency of adjustment of the adjustable valve of this invention may be provided to relieve the burden on the surgeon.

DESCRIPTION OF THE INVENTION

In this invention, a hemostasis valve defines first and second tubular housings, said housings being connected together in axial, telescoping, screw-threaded relation, whereby relative rotation of the housings causes them to advance and retract relative to each other.

The first housing defines a bore which includes an enlarged chamber portion. A tubular, resilient gasket is retained in the enlarged chamber portion. The second housing defines an end portion which projects into the bore of the first housing to press against the tubular, resilient gasket with variable pressures depending on the relative rotational position of the housings.

Thus, a wire member can pass through the bores of the tubular housings and the tubular, resilient gasket, and a variable pressure seal may be applied to the wire at the tubular, resilient gasket by rotational adjustment of the housings. As the housings are brought closer together, they compress the tubular, resilient gasket in longitudinal manner. This, in turn, causes the bore of the tubular gasket to collapse inwardly, pressing against a wire portion that occupies the bore, thus providing a seal which presses against the wire with force that is dependent on the rotational position of the housings.

A second, apertured, resilient gasket, spaced from the tubular, resilient gasket, is also present to provide the valve with a second, low-pressure sealing site for the wire member extending through the aperture of the second gasket. Thus, the same wire member that is sealed with the first tubular, resilient gasket may also extend through the aperture in the second gasket, which is proportioned to be slightly smaller than the diameter of the wire. Thus a second seal may be provided which typically is of relatively low pressure resistance so that it does not seriously interfere with advancement of the wire in the manner described above. Nevertheless, the second seal is sufficient to prevent leakage when the first, tubular, resilient gasket is not being compressed, and thus not providing a strong seal against the wire. Accordingly, the first, tubular, resilient gasket may be intermittently released so as to provide little or no sealing, for advancing the wire member, but still low pressure sealing is provided by the second gasket.

Typically, the second gasket is carried on the second housing. An end piece with a laterally extending handle may hold the second gasket in coaxial relation with the second housing to permit the aperture of the second gasket to align with the bores of the respective housings and the bore of the first, tubular, resilient gasket.

The first housing may define branched, tubular connection means communicating with the bore of the first housing. When the valve of this invention is part of a catheter for entering coronary blood vessels, this branched, tubular connection may be used to insert contrast fluid, where local pressures of injection of the contrast fluid into the system may reach several hundred pounds per square inch.

During this operation, the first, tubular, resilient gasket may be longitudinally compressed between the two housings for high pressure sealing around the advance wire. However, when it is desired to advance the wire, the two housings may be rotated relative to each other to release the high pressure sealing so that advancement of the wire may be facilitated, but the second gasket still provides adequate sealing while the wire is being advanced.

DESCRIPTION OF DRAWINGS

Referring to the drawings.

DESCRIPTION OF SPECIFIC EMBODIMENT

Figure 1:
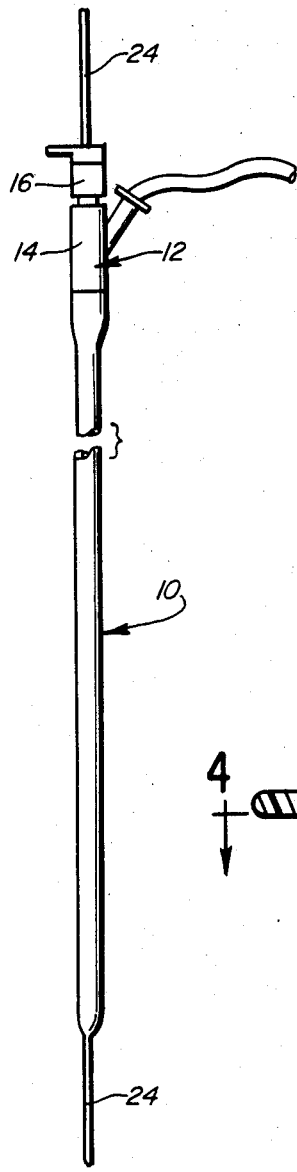
FIG. 1 is a plan view of a catheter for entering coronary blood vessels, carrying the hemostasis valve of this invention.
Figure 2:
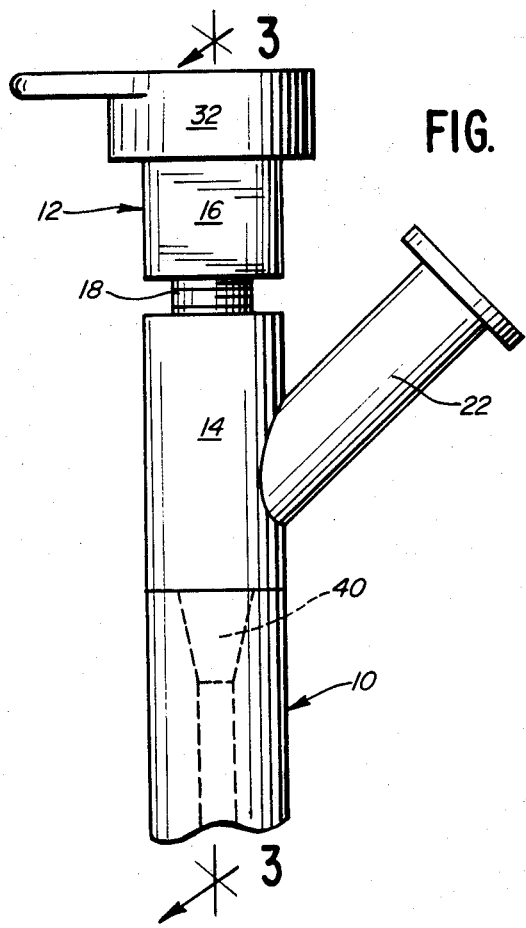
FIG. 2 is a fragmentary, enlarged, elevational view of the catheter of FIG. 1 showing exterior details of the hemostasis valve.
Figure 4:
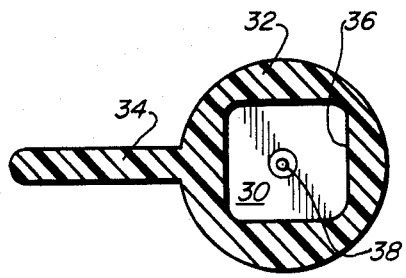
FIG. 4 is a transverse sectional view taken along line 4—4 of FIG. 3.

Referring to the drawings, FIG. 1 shows a catheter 10 for entering coronary blood vessels. Specific details of catheter 10 are not shown since the catheter per se, except as otherwise described herein, may be a catheter for performing an angiographic procedure of conventional design.

Figure 3:
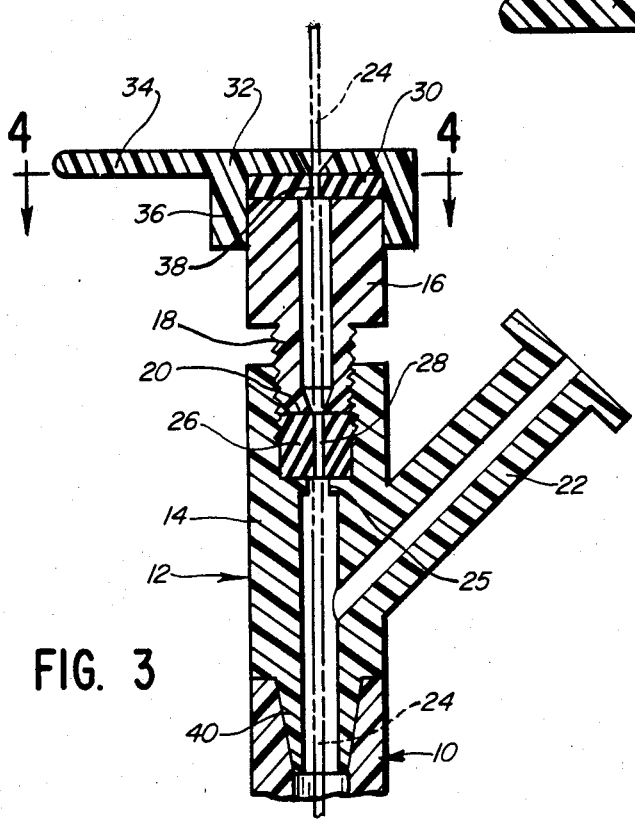
FIG. 3 is a longitudinal sectional view taken along line 3—3 of FIG. 2.

At the proximal end of catheter 10 the mostatsis valve 12 is provided, being of a design in accordance with this invention. Valve 12 defines first tubular housing 14 and second tubular housing 16. As shown in FIG. 3, second housing 16 defines a threaded projection 18 which fits into threaded recess 20 defined in second housing 14 so that relative rotation of the housings causes them to advance and retract relative to each other, depending upon the direction of rotation.

First housing 14 may also have branched tubular connection 22 which may be used for providing fluids, such as x-ray contrast fluid and saline solution to the bore of an angiographic catheter.

Stylet or advancement wire 24 may be stainless steel coated with polytetrafluoroethylene, and may pass through the bores of the respective housings 14, 16 in conventional manner.

As shown in FIG. 3, first housing 14 defines a bore which includes an enlarged chamber portion having annular shoulder 25 for retaining a tubular, resilient gasket 26 in the enlarged chamber portion. As shown, threaded end portion 18 of second housing 16 may press against first tubular, resilient gasket 26 to press it against annular shoulder 25 in a longitudinal direction. The effect of this is to cause bore 28 of first gasket 26 to constrict, with the effect that if wire 24 is present, bore 28 will constrict upon it, forming a seal of relatively high pressure, depending upon the amount of compression given to first gasket 26 by the relative rotational position of housings 14, 16. The pitch of the mating threads of 14 and 16 may be chosen so that a relative rotation of 90° between 14 and 16 will cause 26 to change from the low pressure seal mode to the high pressure seal mode. Stops can be provided on items 14 and 16 so that, often initial assembly, relative rotation between 14 and 16 will be limited to 90° thus making the valve easier to use as its open and closed positions are now defined exactly.

Thus, when a high pressure seal is formed against wire 24 at first gasket 26, high pressure fluids may be injected through side arm 22 into the bore of first housing 14 without leakage through first gasket 26. In the event that a small amount of leakage is detected, one can simply tighten the relationship of housings 14, 16 to provide added sealing pressure.

When the desired fluid has been injected through side arm 22 and the pressure has dropped once again, one may wish to advance wire 24 through catheter 10 again. This is not easily done with a high pressure seal at first gasket 26, because even if wire 24 can be forced through gasket 26, one loses the needed sensitive feel about what the distal end of wire 24 is encountering within a vein or artery of the patient. Accordingly, one may rotate housings 14, 16 to reduce the longitudinal pressure on first gasket 26, with a consequent reduction of the pressure of the seal of the gasket bore 28 against wire 24.

To prevent leakage when the high pressure seal provided by first gasket 26 is released, a second apertured resilient gasket 30 is provided, shown in FIG. 3 to be carried on second housing 16 and held in position by end piece 32. End piece 32 may be made of a rigid plastic material, and may define a laterally extending handle 34 to provide ease in turning second housing 16 relative to first housing 14. End piece 32 may be glued in position on housing 16 and, if desired, housing 16 may have a square or other non-circular cross section, which cross section is matched by mating flange 36 of end piece 32 to prevent rotational slippage between second housing 16 and end piece 32.

Second gasket 30 defines a bore 38, which may be slightly undersized with respect to the diameter of wire 24, to provide a continuous, typically low pressure seal with wire 24. The level of pressure of this seal is generally selected to permit advancement of wire 24 without serious interference with the "sensitive feel" that the surgeon must have as he advances wire 24 into a blood vessel. For example, the diameter of wire 24 may be 0.014 inch. Similarly, the diameter of bore 28 of first gasket 26 may be 0.017 inch when unstressed. The diameter of bore 28, of course, reduces to that of wire 24 with increased pressure, when the high pressure seal is desired. The diameter of bore 38 may be 0.010 inch.

First housing 14 may also define a tapered luer tip 40 to facilitate connection between housing 14 and catheter 10.

Gaskets 26, 30 may be made of any desired elastic material; for example silicone rubber or another similar material suitable for contact with blood.

Hemostasis valve 12 may be modified to receive a dilatation catheter rather than a wire through bores 28, 38, with catheter 10 serving as a blood vessel access catheter.

Accordingly, catheters used in dilation procedures or angiographic catheters, as specific examples, may carry a hemostasis valve which is adjustable to provide desired and variable high pressure sealing, so that blood or other fluid will not escape out the proximal end of the catheter during use. When the high pressure is released, as is generally desired for advancement of wire 24, one can remove the pressure by proper relative rotation of housings 14, 16 without concern that there will be spillage out of the proximal end of the catheter, because of the presence of a constant, typically low pressure seal against wire 24 provided by second gasket 30.

The above has been offered for illustrative purposes only, and is not intended to limit the scope of the invention of this application, which is as defined in the claims below.

That which is claimed is:

1. A hemostasis valve for connection to the proximal end of a catheter, which comprises:
 a first tubular housing defining a central bore and having an inlet end and an outlet end with the outlet end of the first tubular housing being connected to the proximal end of the catheter;

a second tubular housing defining a central bore and having an inlet end and an outlet end and with the outlet end connected to the inlet end of the first tubular housing;

said housing being connected together in axial, telescoping, screw-threaded relation, whereby relative rotation of the housing causes them to advance and retract relative to each other;

one of said housings including an enlarged chamber portion;

a tubular, resilient gasket retained in said enlarged chamber portion;

the other of said housings projecting into said chamber to press against said tubular, resilient gasket with variable pressures depending on the relative rotational position of said housings, whereby a wire member can pass through the bores of said tubular housings and the tubular, resilient gasket and a variable pressure seal may be applied to the wire at the tubular, resilient gasket by rotational adjustment of the housings;

a second apertured resilient gasket, carried on said second tubular housing between the inlet end and outlet end thereof, said second gasket being spaced from said tubular, resilient gasket, to provide the valve with a second, low-pressure sealing site for the wire member extending through the aperture of the second gasket.

2. The valve of claim 1 in which the aperture of the second gasket is coaxially located with the bore of the tubular, resilient gasket and the first and second tubular housings.

3. The valve of claim 1 in which an end piece with a laterally extending handle holds the second gasket in coaxial relation with the second housing.

4. The valve of claim 1 in which said first housing defines branched, tubular connection means communicating with the bore of the first housing.

5. A hemostatis valve as described in claim 1, in which said second gasket does not substantially vary in configuration in response to relative rotation of said housing.

* * * * *